United States Patent

Nadelson

[11] 4,000,307
[45] Dec. 28, 1976

[54] ALKANOYL ISOINDOLINYLMETHYL ALKYLPHENONES

[75] Inventor: Jeffrey Nadelson, Lake Parsippany, N.J.

[73] Assignee: Sandoz, Inc., E. Hanover, N.J.

[22] Filed: Nov. 19, 1975

[21] Appl. No.: 633,170

[52] U.S. Cl. .......................... 424/274; 260/326 A; 260/326.1; 260/340.7; 260/592

[51] Int. Cl.² .................. C07D 209/44; A61K 31/40

[58] Field of Search ................. 260/326.1; 424/274

[56] References Cited

UNITED STATES PATENTS

| | | | |
|---|---|---|---|
| 3,856,812 | 12/1974 | Dahm et al. | 260/326.1 |
| 3,862,936 | 1/1975 | Geschickter | 260/326.1 |
| 3,892,770 | 7/1975 | Dahm et al. | 260/326.1 |

Primary Examiner—Lewis Gotts
Assistant Examiner—S. P. Williams
Attorney, Agent, or Firm—Gerald D. Sharkin; Robert S. Honor; Thomas O. McGovern

[57] ABSTRACT

Alkanoyl isoindolinylmethyl alkylphenones of the formula,

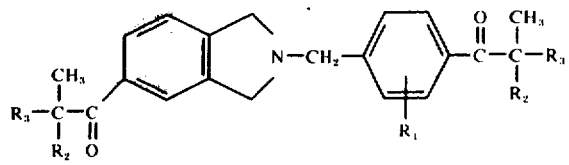

e.g. 4'-(5-pivaloyl-2-isoindolinylmethyl)-pivalophenone, are prepared by reacting a 3',4'-bis(bromomethyl)alkylphenone with a 4'-(aminomethyl)alkylphenone-(2,2-dimethyl-1,3-propanediyl)cyclic ketal and hydrolyzing the ketal formed, and are useful as hypolipidemic agents.

8 Claims, No Drawings

ALKANOYL ISOINDOLINYLMETHYL ALKYLPHENONES

This invention relates to alkanoyl isoindolinylmethyl alkylphenones, which exhibit hypolipidemic activity. More particularly, it relates to alkanoylisoindolinyl methyl alkylphenones, intermediates and certain pharmaceutically acceptable salts thereof, and to methods for their preparation.

The compounds of this invention may be represented by the following structural formula:

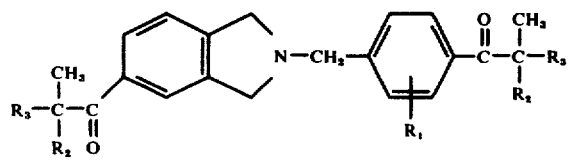

(I)

where
  $R_1$ represents hydrogen or halo having an atomic weight of about 19 to 36, and
  $R_2$ and $R_3$ each independently represent lower alkyl having 1 to 2 carbon atoms, i.e. methyl or ethyl.

The compounds of formula (I) are prepared according to the following reaction scheme:

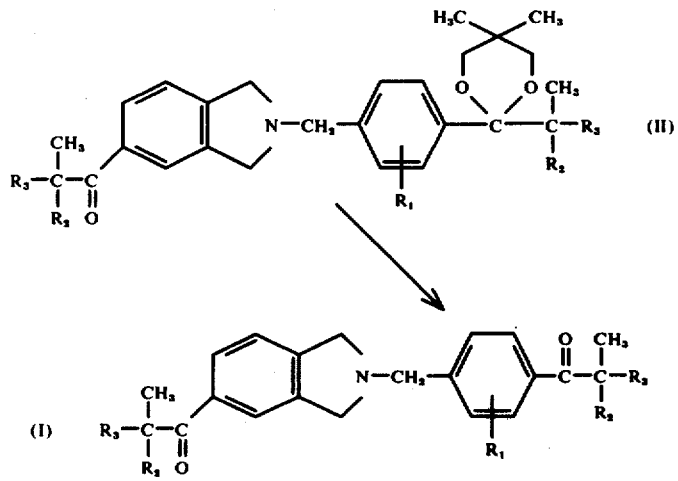

where
  $R_1$, $R_2$ and $R_3$ are as defined above.

The compounds of formula (I) are prepared by hydrolyzing a compound of the formula (II) in the presence of an acid and an aqueous solvent. Although the particular acid employed is not critical, it is preferred that the reaction be run in the presence of an acid such as acetic acid, p-toluenesulfonic acid, polyphosphoric acid, sulfuric acid or hydrochloric acid, the latter being especially preferred. The particular solvent employed is also not critical, although it is preferred that the reaction be carried out in the presence of an aqueous solvent such as water or a mixture of water and water soluble organic solvent, or an excess of the acid utilized above, preferably water. The temperature of the reaction is not critical, but it is preferred that the reaction be run from about 50° to 150° C., preferably the reflux temperature of the solvent. The reaction is run from about 1 to 10 hours, preferably from about 2 to 4 hours. The product is recovered using conventional techniques, e.g., filtration.

The compounds of formula (II) are prepared according to the following reaction scheme:

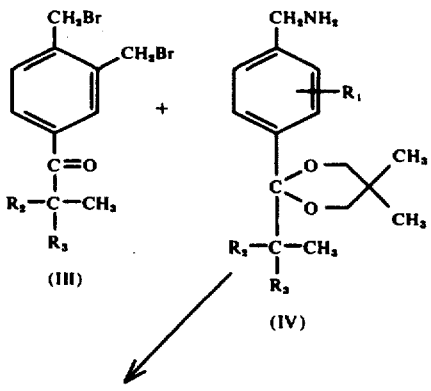

-continued

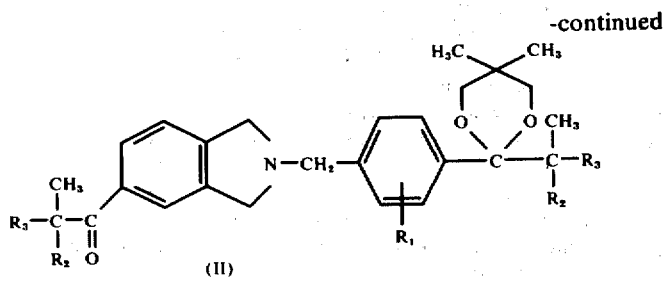

(II)

where
R₁, R₂ and R₃ are as defined above.

The compounds of formula (IV) are prepared according to the following reaction scheme:

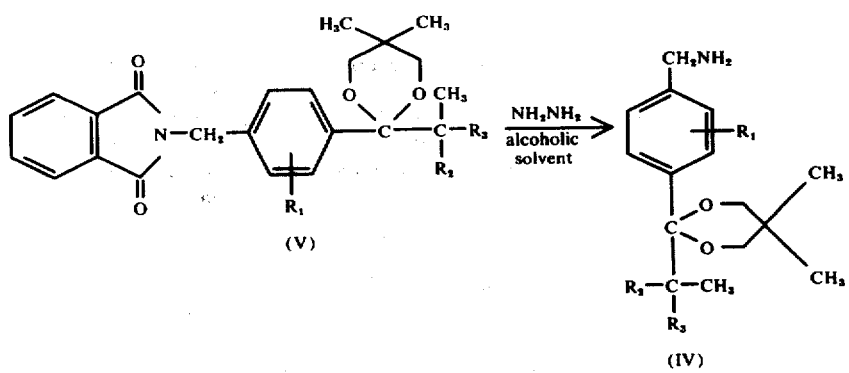

The compounds of formula (II) are prepared by reacting a compound of the formula (III) with a compound of the formula (IV) in the presence of a hydrogen bromide scavenger such as pyridine, triethylamine or N,N-diisopropyl ethylamine, the latter being especially preferred, and an inert organic solvent. Although the particular solvent employed is not critical, it is preferred that the reaction be carried out in the presence of an aromatic hydrocarbon, such as benzene, toluene and the like, diethylether or tetrahydrofuran, preferably benzene. The temperature of the reaction is not critical, but it is preferred that the reaction be run from about 25° to 150° C., preferably the reflux temperature of the solvent. The reaction is run from about 5 to 24 hours, preferably 16 to 22 hours. The product (II) is not recovered but employed in situ. However, it is to be noted that compounds (II) could have been recovered using conventional techniques, e.g. filtration.

where
R₁, R₂ and R₃ are as defined above.

The compounds of formula (IV) are prepared by reacting a compound of the formula (V) with hydrazine in the presence of an alcoholic solvent. Although the particular alcoholic solvent employed is not critical, it is preferred that the reaction be carried out in the presence of a lower alkanol such as methanol, ethanol and the like, or an alkoxy alcohol such as 2-methoxymethanol, or 2-methoxyethanol, preferably methanol. The temperature of the reaction is not critical, but it is preferred that the reaction be run from about 60° to 180° C., preferably the reflux temperature of the solvent. The reaction is run from about 1 to 10 hours, preferably from about 2 to 4 hours. The product is recovered using conventional techniques, e.g., filtration followed by evaporation.

The compounds of formula (V) are prepared according to the following reaction scheme:

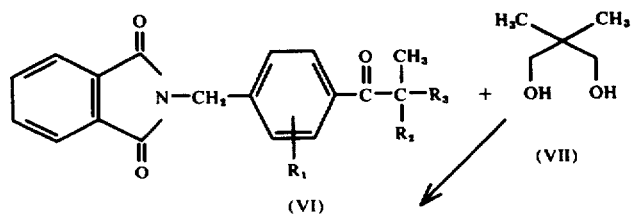

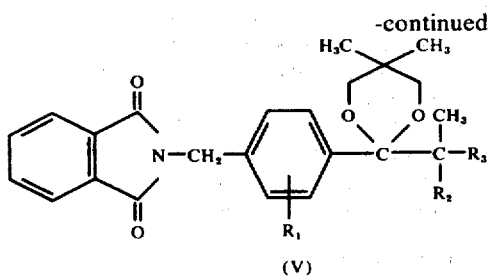

(V)

where

R₁, R₂ and R₃ are as defined above.

The compounds of formula (V) are prepared by reacting a compound of the formula (VI) with a compound of the formula (VII) in the presence of an acid catalyst such as hydrochloric acid, sulfuric acid, polyphosphoric acid or p-toluenesulfonic acid, the latter being especially preferred and in the presence of an inert organic solvent. It is preferred that the reaction be carried out in the presence of an aromatic hydrocarbon such as benzene, toluene and the like, tetrahydrofuran, diethylether or dioxane, preferably toluene. The temperature of the reaction is not critical, but it is preferred that the reaction be run from about 60° to 180° C., preferably the reflux temperature of the solvent. The reaction is run from about 18 to 72 hours, preferably from about 45 to 55 hours. The product is recovered using conventional techniques, e.g., filtration.

The compounds of formula (VI) are prepared according to the following reaction scheme:

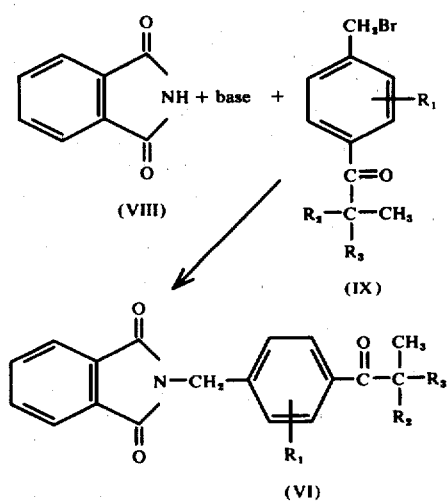

where

R₁, R₂ and R₃ are as defined above.

The compounds of formula (VI) are prepared by first treating a compound of the formula (VIII) with a strong base such as an alkali metal hydride, e.g. sodium hydride, potassium hydride, or lithium hydride, or an alkali metal hydroxide such as potassium hydroxide, sodium hydroxide and the like in the presence of an inert organic solvent. The particular solvent employed is not critical, but it is preferred that the reaction be carried out in dimethylacetamide, dimethylformamide, an aromatic hydrocarbon such as benzene, toluene and the like, tetrahydrofuran or dioxane, preferably dimethylacetamide. The temperature of the reaction is not critical, but it is preferred that the reaction be run at a temperature of from about 20° to 80° C., preferably from about 25° to 35° C. The reaction is run from about 1 to 5 hours, preferably from about 1½ to 2½ hours. The product obtained from the above step is then reacted with a compound of the formula (IX) in the presence of an inert organic solvent. The particular solvent employed is not critical, but it is preferred that the reaction be run in the presence of an aromatic hydrocarbon such as benzene, toluene and the like, dimethylacetamide, or dimethylformamide, preferably dimethylacetamide. The reaction is typically run at a temperature of from about 20° to 80° C., preferably from about 25° to 35° C. The reaction may be run from about 10 to 30 hours, preferably from about 16 to 22 hours. The product is recovered using conventional techniques, e.g. filtration.

Another aspect of this invention is the preparation of the compounds of formula (III) according to the following reaction scheme:

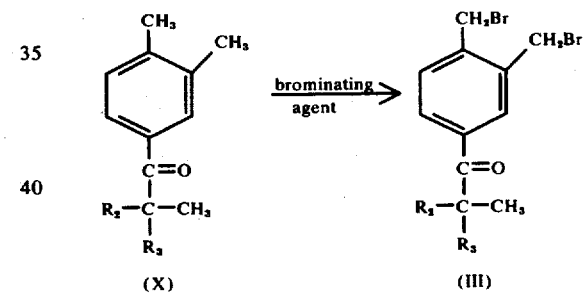

where

R₂ and R₃ are as defined above.

The compounds of formula (III) are prepared by treating a compound of the formula (X) with an excess of brominating agent in the presence of an inert organic solvent and free radical initiator. It is preferred that the reaction be carried out in the presence of 2 to 4 moles of brominating agent, more preferably 2 to 3 moles of brominating agent. The brominating agent which can be used is bromide, N-bromosuccinimide, N-bromophthalamide, N-bromo-acetamide and the like. The particular agent used is not critical but N-bromosuccinimide is preferred. In the preferred process, the free radical initiator used is an organic or inorganic peroxide, especially benzoyl peroxide. The reaction can also be carried out under ultraviolet light. Although the particular solvent employed is not critical, the preferred solvents include the halogenated hydrocarbons such as methylene dichloride, chloroform, carbon tetrachloride and the like, although the aromatic hydrocarbons such as benzene, and the like, may also be employed. The temperature of the reaction is not critical, but reflux temperature of the solvent is preferred.

The reaction is run from about 12 to 48 hours, preferably from about 18 to 25 hours. The product is recovered by conventional techniques, e.g. crystallization.

Many of the compounds of formulae (VII), (VIII), (IX) and (X) are known and may be prepared by methods described in the literature. The compounds of formulae (VII), (VIII), (IX) and (X) not specifically described may be prepared by analogous methods from known starting materials.

The compounds of formulae (I), (II) and (IV) may also exist as acid addition salts, and are readily prepared by reacting the base with an appropriate acid by conventional techniques.

The compounds of formula (I) are useful because they possess pharmacological activity in animals as hypolipidemic agents, as indicated by the fall in cholesterol and triglyceride levels in male albino Wistar rats weighing 110–130g. initially. The rats are maintained on drug-free laboratory chow diet for seven days and then divided into groups of 8 to 10 animals. Each group with the exception of the control is then given orally 120 milligrams per kilogram of body weight per diem of the compound for 6 days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in the cholesterol levels as a percentage of the control level. The change in serum triglyceride levels induced by the drug is computed as a percentage of the control triglyceride levels.

For such usage, the compounds (I) may be combined with a pharmaceutically acceptable carrier of adjuvant and may be administered orally or parenterally as such or admixed with conventional pharmaceutical carriers. The may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free base and are readily prepared by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 7.0 milligrams to about 250 milligrams per kilogram of animal body weight, preferably given in divided doses two to four times a day, or in sustained release form. For most large mammals, the total daily dosage is from about 500 milligrams to about 2500 milligrams. Dosage forms suitable for internal use comprise from about 125 to about 1250 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg.) |
|---|---|
| 4'-(5-pivaloyl-2-isoindolinylmethyl) pivalophenone | 150 |
| inert solid diluent (starch, lactose, kaolin | 300 |

EXAMPLE I

3',4'-dimethylpivalophenone

A suspension of 25.9 g. (0.15 mole) of phenyl thio copper in 1 liter dry tetrahydrofuran is cooled to −20° C. and treated by the dropwise addition of 120 ml. t-butyl lithium (0.149 mole, 1.24 M in pentane) for about 20 minutes maintaining the temperature at −20° C. The resulting green solution is stirred at −20° C. for 5 minutes and then cooled to −72° C. and treated by the dropwise addition of 17.8 g. (0.107 mole) 3,4-dimethyl-benzoyl chloride in 50 ml. tetrahydrofuran for about 20 minutes. The mixture is then stirred at −22° C. for 1½ hours and then treated with 100 ml. methanol and allowed to warm to room temperature and then hydrolyzed by the addition of 250 ml. saturated ammonium chloride. The resulting solids are filtered and washed with tetrahydrofuran. The filtrate is dried over anhydrous magnesium sulfate, filtered and evaporated and the oil distilled to give 3',4'-dimethyl-pivalophenone; (b.p. 73°–76° C. at 0.1 mm).

EXAMPLE II

3',4'-bis-(bromomethyl)pivalophenone

A mixture of 14.1 g. (0.074 mole) of 3',4'-dimethyl-pivalophenone, 26.4 g. (0.148 mole) of N-bromosuccinimide, 0.2 g. benzoyl peroxide and 150 ml. carbon tetrachloride is refluxed until the succinimide floats to the surface. The resulting mixture is filtered and the solid washed with carbon tetrachloride. The solvents are removed in vacuo and the resulting oil crystallized from petroluem ether/ether to give 3',4'-bis(bromomethyl)pivalophenone, m.p. 50°–58° C.

EXAMPLE III

4'-(phthalimidomethyl)pivalophenone

A suspension of 22.4 g. (0.447 mole) of sodium hydride (50% in mineral oil) in 200 ml. dimethylacetamide is treated dropwise by the addition of 59.6 g. (0.406 mole) phthalimide in 500 ml. dimethylacetamide. The mixture is stirred for 2 more hours at room temperature and then treated dropwise with 100 g. (0.406 mole) α-bromo-p-pivaloyl toluene in 300 ml. dimethylacetamide. The resulting mixture is stirred at room temperature for 18 hours and then the solvent is removed in vacuo. The residue is taken up in methylene chloride/water and the layers separated. The water layer is washed twice with methylene chloride and the combined methylene chloride layers washed twice with water, dried over anhydrous magnesium sulfate, filtered and evaporated. The resulting solid is triturated with ether to give 4'-(phthalimidomethyl)pivalophenone; m.p. 138°–140.5° C.

Following the above procedure and using in place of α-bromo-p-pivaloyl toluene an equivalent amount of
 a. α-bromo-2-chloro-4-pivaloyl toluene, or
 b. α-bromo-2-fluoro-4-pivaloyl toluene,
there is obtained
 a. 4'-(phthalimidomethyl)-3'-chloro-pivalophenone, or
 b. 4'-(phthalimidomethyl)-3'-fluoro-pivalophenone, respectively.

EXAMPLE IV

4'-(phthalimidomethyl)pivalophenone-(2,2-dimethyl-1,3-propanediyl)cyclic ketal

A mixture of 21.2 g. (0.222 mole) of 4'-(phthalimidomethyl)-pivalophenone, 34.5 g. (0.331 mole) of 2,2-dimethyl-1,3-propanediol, 0.4 g. p-toluene sulfonic acid and 700 ml. toluene is refluxed under a dean-stark trap for 48 hours. The mixture is then cooled and the solvents removed in vacuo, the resulting solid is slurried in water/ether, filtered and washed thoroughly with water and then ether to give 4'-(phthalimidomethyl)pivalophenone-(2,2-dimethyl-1,3-propanediyl)cyclic ketal; m.p. 250° to 251.5° C.

Following the above procedure and using in place of 4'-(phthalimidomethyl) pivalophenone an equivalent amount of
 a. 4'-(phthalimidomethyl)-3'-chloro-pivalophenone
 b. 4'-(phthalimidomethyl)-3'-fluoro-pivalophenone
there is obtained
 a. 4'-(phthalimidomethyl)-3'-chloro-pivalophenone-(2,2-dimethyl-1,3-propanediyl)cyclic ketal, or
 b. 4'-(phthalimidomethyl)-3'-fluoro-pivalophenone-(2,2-dimethyl-1,3-propanediyl)cyclic ketal, respectively.

EXAMPLE V

4'-(aminomethyl)pivalophenone-(2,2-dimethyl-1,3-propanediyl)cyclic ketal

A mixture of 82.5 g. (0.202 mole) of 4'-(phthalimidomethyl)pivalophenone-(2,2-dimethyl-1,3-propanediyl) cyclic ketal, 61.2 g. (1.22 mole) of hydrazine hydrate and 800 ml. methanol is refluxed for 2 hours. The solvent is removed in vacuo and the residue treated with water/ether and made basic with 2N sodium hydroxide. The ether layer is then separated and the water washed once with ether and the ether layers combined, dried over anhydrous magnesium sulfate, filtered and evaporated in vacuo to give 4'-(aminomethyl)pivalophenone-(2,2-dimethyl)-1,3-propanediyl)cyclic ketal; m.p. 100° to 103° C.

Following the above procedure and using in place of 4'-(phthalimidomethyl)pivalophenone-(2,2-dimethyl-1,3-propanediyl)cyclic ketal an equivalent amount of
 a. 4'-(phthalimidomethyl)-3'-chloro-pivalophenone-(2,2-dimethyl-1,3-propanediyl)cyclic ketal, or
 b. 4'-(phthalimidomethyl)-3'-fluoro-pivalophenone-(2,2-dimethyl-1,3-propanediyl)cyclic ketal
there is obtained
 a. 4'-(aminomethyl)-3'-chloro-pivalophenone-(2,2-dimethyl-1,3-propanediyl)cyclic ketal, or
 b. 4'-(aminomethyl)-3'-fluoro-pivalophenone-(2,2-dimethyl-1,3-propanediyl)cyclic ketal, respectively.

EXAMPLE VI

4'-(5-pivaloyl-2-isoindolinylmethyl)pivalophenone

A solution of 9.29 (0.027 mole) of 3',4'-bis(-bromomethyl)pivalophenone in 100 ml. benzene is cooled to 0° and treated dropwise with 7.4 g. (0.027 mole) of 4'-(aminomethyl) pivalophenone-(2,2-dimethyl-1,3-propanediyl)cycic ketal and 7.4 g. (0.054 mole) of N,N-diisopropylethylamine in 50 ml. of benzene for about 15 minutes. The resulting mixture is stirred at room temperature for 1 hour, refluxed for 4 hours and then stirred at room temperature for 18 hours. The solids are removed by filtration, washed with benzene and the benzene removed in vacuo. The resulting oil identified as 4'-(5-pivaloyl-2-isoindolinylmethyl)pivalophenone-(2,2-dimethyl-1,3-propanediyl)cyclic ketal is suspended in concentrated hydrochloric acid and refluxed for 2 hours. The resulting mixture is cooled and filtered and the solid washed with water to give 4'-(5-pivaloyl-2-isoindolinylmethyl)pivalophenone hydrochloride; m.p. 251° to 253° C.

Following the above procedure and using in place of 4'-(aminomethyl)pivalophenone-(2,2-dimethyl-1,3-propanediyl)cyclic ketal an equivalent amount of
 a. 4'-(aminomethyl)-3'-chloro-pivalophenone-(2,2-dimethyl-1,3-propanediyl)cyclic ketal, or
 b. 4'(aminomethyl)-3'-fluoro-pivalophenone-(2,2-dimethyl-1,3-propanediyl)cyclic ketal
there is obtained
 a. 4'-(5-pivaloyl-2-isoindolinylmethyl)-3'-chloro-pivalophenone hydrochloride, or
 b. 4'-(5-pivaloyl-2-isoindolinylmethyl)-3'-fluoropivalophenone hydrochloride, respectively.

The 4'-(5-pivaloyl-2-isoindolinylmethyl)pivalophenone of this example is an effective hypolipidemic agent when orally administered to an animal suffering from lipideia at a dosage of 150 mg. four times per day.

What is claimed is:

1. A compound of the formula

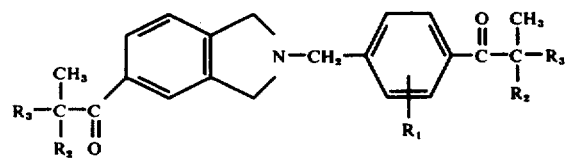

where
 $R_1$ represents hydrogen, halo having an atomic weight of about 19 to 36, and
 $R_2$ and $R_3$ each independently represent lower alkyl having 1 to 2 carbon atoms,
or a pharmaceutically acceptable acid addition salt thereof.

2. A compound of the formula

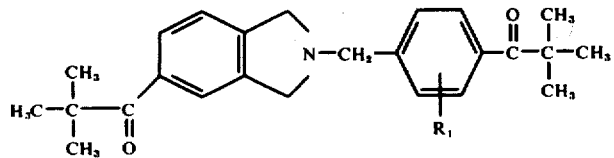

where
R₁ is as defined in claim 1, or a pharmaceutically acceptable acid addition salt thereof.

3. The compound of claim 2 which is 4'-(5-pivaloyl-2-isoindolinylmethyl)pivalophenone hydrochloride.

4. The compound of claim 2 which is 4'-(5-pivaloyl-2-isoindolinylmethyl)pivalophenone.

5. A compound of the formula

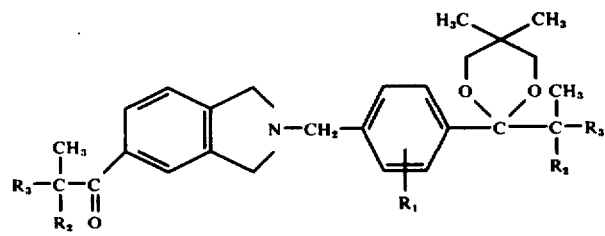

where
R₁, R₂ and R₃ are as defined in claim 1, or an acid addition salt thereof.

6. The compound of claim 5 which is 4'-(5-pivaloyl-2-isoindolinylmethyl)pivalophenone-(2,2-dimethyl-1,3-propanediyl)cyclic ketal.

7. A pharmaceutical composition comprising a compound of claim 1 and a pharmaceutically acceptable diluent or carrier therefor.

8. A method of treating lipidemia which comprises administering to mammal in need of said treatment a hypolipidemic effective amount of a compound of claim 1.

* * * * *